United States Patent [19]
Cuzzato et al.

[11] Patent Number: 5,880,316
[45] Date of Patent: Mar. 9, 1999

[54] PROCESS FOR PREPARING 1,1,1,2-TETRAFLUOROETHANE

[75] Inventors: Paolo Cuzzato, Treviso; Antonio Masiero, Padua, both of Italy

[73] Assignee: Ausimont S.p.A., Italy

[ * ] Notice: The term of this patent shall not extend beyond the expiration date of Pat. Nos. 5,463,151 and 5,608,125.

[21] Appl. No.: 752,685

[22] Filed: Nov. 19, 1996

Related U.S. Application Data

[63] Continuation of Ser. No. 507,644, Jul. 25, 1995, Pat. No. 5,608,125, which is a continuation of Ser. No. 337,128, Nov. 10, 1994, Pat. No. 5,463,151, which is a continuation of Ser. No. 191,765, Feb. 3, 1994, abandoned, which is a continuation of Ser. No. 928,188, Aug. 14, 1992, abandoned, which is a continuation of Ser. No. 811,920, Dec. 23, 1991, abandoned, which is a continuation of Ser. No. 550,559, Jul. 10, 1990, abandoned.

[30] Foreign Application Priority Data

Jul. 12, 1989 [IT] Italy .................................. 21159 A/89

[51] Int. Cl.$^6$ .................................................. C07C 17/08
[52] U.S. Cl. ........................................... 570/166; 570/169
[58] Field of Search ...................................... 570/166, 169

[56] References Cited

U.S. PATENT DOCUMENTS

| | | |
|---|---|---|
| 1,914,135 | 6/1933 | Lacy . |
| 2,005,708 | 6/1935 | Daudt et al. . |
| 2,399,024 | 4/1946 | Harmon . |
| 2,402,854 | 6/1946 | Thomas . |
| 2,426,172 | 8/1947 | Benning . |
| 2,458,551 | 1/1949 | Benning . |
| 2,480,560 | 8/1949 | Downing et al. . |
| 2,490,764 | 12/1949 | Benning et al. . |
| 2,637,747 | 5/1953 | McBee . |
| 2,739,989 | 3/1956 | Barringer . |
| 2,744,147 | 5/1956 | Milks . |
| 2,744,148 | 5/1956 | Ruh et al. . |
| 2,745,867 | 5/1956 | Ruh et al. . |
| 2,745,886 | 5/1956 | Ruh et al. . |
| 2,885,427 | 5/1959 | Ruh et al. . |
| 2,946,827 | 7/1960 | Belf et al. . |
| 2,951,102 | 8/1960 | Larsen et al. . |
| 3,003,003 | 10/1961 | McGinty . |
| 3,240,826 | 3/1966 | Davis . |
| 3,258,500 | 6/1966 | Swamer et al. . |
| 3,287,424 | 11/1966 | Pacini et al. . |
| 3,426,009 | 2/1969 | Chapman et al. . |
| 3,660,307 | 5/1972 | Scherer et al. . |
| 3,697,443 | 10/1972 | Shinoda ................................ 570/166 |
| 3,752,850 | 8/1973 | Scherer . |
| 3,755,477 | 8/1973 | Firth et al. . |
| 3,803,241 | 4/1974 | Doebendorf et al. . |
| 3,843,546 | 10/1974 | Sobolev et al. . |
| 3,859,424 | 1/1975 | Scherer et al. . |
| 3,978,145 | 8/1976 | Knaak et al. . |
| 3,992,325 | 11/1976 | Knaak . |
| 4,088,704 | 5/1978 | Nychka . |
| 4,129,603 | 12/1978 | Bell . |
| 4,158,675 | 6/1979 | Potter . |
| 4,258,225 | 3/1981 | Feiring . |
| 4,311,863 | 1/1982 | Gumprecht . |

(List continued on next page.)

FOREIGN PATENT DOCUMENTS

| | | |
|---|---|---|
| 863913 | 8/1978 | Belgium . |
| 1 124 265 | 5/1982 | Canada . |
| 1 196 345 | 11/1985 | Canada . |
| 0 295 885 A1 | 12/1988 | European Pat. Off. . |
| 0 300 724 A1 | 1/1989 | European Pat. Off. . |
| 0 328 127 A1 | 8/1989 | European Pat. Off. . |
| 0 331 991 A1 | 9/1989 | European Pat. Off. . |
| 0 408 005 A1 | 1/1991 | European Pat. Off. . |
| 0 446 869 A1 | 9/1991 | European Pat. Off. . |
| 0 449 614 A2 | 10/1991 | European Pat. Off. . |
| 0 449 617 A2 | 10/1991 | European Pat. Off. . |
| 0 502 605 A1 | 9/1992 | European Pat. Off. . |
| 0 408 005 B1 | 3/1994 | European Pat. Off. . |
| 1 383 927 | 1/1965 | France . |
| 2 381 006 | 9/1978 | France . |
| 1 246 703 | 8/1967 | Germany . |
| 1 950 804 | 10/1970 | Germany . |
| 2 128 341 | 12/1971 | Germany . |
| 2 932 934 | 8/1979 | Germany . |
| 1246703 | 8/1987 | Germany ............................. 570/169 |
| 55-27138 | 2/1980 | Japan . |
| 640486 | 7/1950 | United Kingdom . |
| 819849 | 9/1959 | United Kingdom . |
| 881003 | 11/1961 | United Kingdom . |
| 1000485 | 8/1965 | United Kingdom . |
| 2004539 | 4/1979 | United Kingdom . |
| 2030981 | 4/1980 | United Kingdom . |
| 1578933 | 11/1980 | United Kingdom . |
| WO 90/08755 | 8/1990 | WIPO . |

OTHER PUBLICATIONS

Luft, "Torsional Barriers In Molecules $C_2H_mF_nCl_{6-m-n}$" *J.Phys.Chem.*, vol. 59, pp. 92–93 (Jan. 1955).

Houben–Weyl, *Methoden Der Organischen Chemie*, vol. V/3, pp. 135–140, (4th ed. 1962).

Staritzky, "Aluminum Trifluoride, $AiF_3$," *Anal. Chem.* vol. 29, p. 984 (1957).

Hudlicky, *Chemistry of Organic Fluorine Compounds*, p. 93 (1962).

Cuculo, "The Action of Elementary Fluorine upon Organic Compounds. XVII. The Direct Fluorination of Acetonitrile," *JACS*, vol. 74, pp. 710–713 (Feb. 2, 1952).

*Primary Examiner*—Alan Siegel
*Attorney, Agent, or Firm*—Bryan Cave LLP

[57] ABSTRACT

1,1,1,2-tetrafluoroethane (134a) is prepared by reacting, in the gas phase, trichloroethylene with 1,1,1-trifluorochloroethane (133a) and hydrofluoric acid with trichloroethylene/133a molar ratios ranging from 5/95 to 50/50, in the presence of a catalyst consisting of $Cr_2O_3$ carried on $AlF_3$.

The process provides 134a yields higher than 90% and permits an exceptionally long life of the catalyst. In this way it is possible to realize a continuous process by recycling the unreacted trichloroethylene and 133a, thereby making up for the relatively low global conversion of the reagents.

20 Claims, No Drawings

U.S. PATENT DOCUMENTS

| | | |
|---|---|---|
| 4,754,085 | 6/1988 | Gervasuti et al. . |
| 4,766,258 | 8/1988 | Manzer et al. . |
| 4,766,259 | 8/1988 | Manzer et al. . |
| 4,766,260 | 8/1988 | Manzer et al. . |
| 4,792,643 | 12/1988 | Sobelov . |
| 4,843,181 | 6/1989 | Gumprecht et al. . |
| 4,851,595 | 7/1989 | Gumprecht . |
| 4,861,744 | 8/1989 | Sobolev . |
| 4,906,796 | 3/1990 | Yates . |
| 4,922,037 | 5/1990 | Manzer ................................. 570/166 |
| 4,950,815 | 8/1990 | Moore et al. . |
| 4,990,701 | 2/1991 | Cassel et al. . |
| 4,990,702 | 2/1991 | Fernandez et al. . |
| 4,996,379 | 2/1991 | Oshio et al. . |
| 5,001,287 | 3/1991 | Fernandez et al. . |
| 5,008,475 | 4/1991 | Manzer et al. . |
| 5,026,930 | 6/1991 | Manzer et al. . |
| 5,051,537 | 9/1991 | Manzer . |
| 5,091,600 | 2/1992 | Moore et al. . |
| 5,155,082 | 10/1992 | Tung et al. . |
| 5,171,900 | 12/1992 | Eicher et al. . |
| 5,185,482 | 2/1993 | Manzer . |
| 5,214,223 | 5/1993 | Eicher et al. . |
| 5,243,104 | 9/1993 | Yamaguchi et al. . |
| 5,243,105 | 9/1993 | Scott et al. . |
| 5,243,107 | 9/1993 | Scott et al. . |
| 5,345,016 | 9/1994 | Manzer . |

PROCESS FOR PREPARING 1,1,1,2-TETRAFLUOROETHANE

This is a continuation, of U.S. Application Ser. No. 08/507,644, filed Jul. 25, 1995, now U.S. Pat. No. 5,608,125, which is a continuation of U.S. Application Ser. No. 08/337,128, filed Nov. 10, 1994, now U.S. Pat. No. 5,463,151, which is a continuation of U.S. Application Ser. No. 08/191,765, filed Feb. 3, 1994 (now abandoned), which is a continuation of U.S. Application Ser. No. 07/928,188, filed Aug. 14, 1992 (now abandoned), which is a continuation of U.S. Application Ser. No. 07/811,920, filed Dec. 23, 1991 (now abandoned), which is a continuation of U.S. Application Ser. No. 07/550,559, filed Jul. 10, 1990 (now abandoned).

DESCRIPTION OF THE INVENTION

The present invention relates to a process for preparing, in the gas phase, 1,1,1,2-tetrafluoroethane by reaction of trichloroethylene ($CHCl=CCl_2$) with hydrofluoric acid in the presence of catalysts.

It is known that it is possible to obtain 1,1,1,2-tetrafluoroethane (hereinafter referred to as 134a) by catalytic reaction in the gas phase between 1,1,1-trifluorochloroethane (hereinafter referred to as 133a) and hydrofluoric acid according to the reaction:

$$CF_3-CH_2Cl \xrightarrow{HF} CF_3-CH_2F$$

According to U.S. patent No. 4,129,603, said reaction is made to occur by using a catalyst consisting of chrome oxide or, at least partially, of basic chrome fluoride, at temperatures ranging from 300° to 400° C., thereby obtaining 133a conversions of 20%, with yields of 134a equal to 91%.

According to said process, also $CF_2=CHCl$ forms (in consequence of 133a dehydrofluorination), the boiling point of which, which is higher by only 9° C. than the boiling point of 134a, makes the separation thereof difficult and anti-economic.

Thus, Belgian patent No. 863,913 describes a method for reducing or eliminating the abovesaid impurity from the reaction products, which consists in the olefin post-fluorination carried out at low temperature with the same type of catalyst.

According to another method, described in Canadian patent No. 1,124,265, such olefin content is reduced to 5–10 ppm by contacting the 133a fluorination products with an aqueous solution of $KMnO_4$.

Other processes for preparing 134a by means of fluorination of 133a with catalysts based on chrome oxide are described in Japan patent application No. 80-27138 and in German patent application No. 2,932,934, according to which applications, conversions of 21% and 31%, with 134a yields of 91% and 98%, are respectively obtained.

European patent No. 300,724 described a process for preparing in the liquid phase, 134a by fluorination of 133a in the presence of catalysts based on antimonium halides. Said process is affected by the drawback of not being highly selective, in particular owing to the considerable pentafluoroethane amount produced. In said process, mention is made of the difficulty to produce 134a through fluorination, in the gas phase, of trichloroethylene.

In fact, the Applicant has ascertained by means of tests, that the direct fluorination of trichloroethylene in the gas phase using, for example, a chrome oxyfluoride catalyst, produces 134a with yields of only 3%, although it provides high yields of 133a and trichloroethylene conversions of 92%.

Furthermore, the catalyst activity rapidly decays, wherefore such a process, if it were utilized to produce 134a with acceptable yields, would require frequent reactivations of the catalyst, to the prejudice of its applicability on an industrial scale.

An alternative would be that of preparing separately 133a by fluorination of trichloroethylene in the liquid phase and of using it for preparing 134a through fluorination in the gas phase.

This solution, however, would result in a considerable industrial burden, as two distinct plants with two different technologies would be required.

The Applicant has now found that it is possible to realize an industrial process in the gas phase for preparing 134a with industrially acceptable conversions, the process being furthermore highly selective, by reacting a mixture of trichloroethylene and 133a in trichloroethylene/133a molar ratios ranging from 5/95 to 50/50 with hydrofluoric acid, in the presence of a catalyst consisting of $Cr_2O_3$ carried on aluminium trifluoride.

In such process, which is the object of the present invention, the catalyst surprisingly retains its full activity for very long stretches of time, of the order of hundreds of hours, thereby permitting to realize the process on an industrial scale, continuously.

A preferred mode of carrying out the abovesaid process consists in feeding, at the beginning, the reactor containing the catalyst with the trichloroethylene and 133a mixture along with hydrofluoric acid in the above-mentioned ratios, in separating, at the reactor outlet, the 134a, which has formed, from the other reaction products, prevailingly consisting of 133a, and in recycling said products to the reactor after addition of trichloroethylene and hydrofluoric acid in order to restore the reagents in the above-indicated ratios.

The reaction among trichloroethylene, 133a and hydrofluoric acid is preferably conducted at temperatures from 300° to 400° C., and even more preferably at temperatures from 330° to 380° C., at atmospheric pressure or also at higher pressures, up to 15 atmospheres.

Preferred feeding conditions utilize trichloroethylene/133a molar ratios of about 15/85. Generally it is operated with HF/trichloroethylene+133a molar ratios not lower than 3, while particularly critical upper values of such ratio do not exist. However, it is preferable to operate with HF/trichloroethylene+133a molar ratios ranging from 3/1 to 10/1 and, even more preferably, from 4/1 to 6/1.

The contact time between reagents and catalyst is not critical above a minimum threshold of one second. Usually it is operated with contact times ranging from 1 second to 50 seconds, and preferably from 5 to 20 seconds.

The process can be conducted both discontinuously, collecting the reaction products after only one run on the catalyst, and continuously, recycling the unreacted trichloroethylene and the 133a to the reactor, after having restored the reagents amount in the above-defined ratios, as mentioned hereinbefore.

The catalyst to be used in the process of the invention is composed, as mentioned above, of chrome trioxide carried on $AlF_3$ in the gamma and/or beta form.

The $Cr_2O_3$ amount generally ranges from 1 to 15% by weight, calculated as Cr on the carried catalyst. The percent of $Cr_2O_3$ is a function of the surface area of $AlF_3$ in the gamma form.

Carriers having a great surface area, of the order of 25–30 m$^2$/g, are generally preferred.

The carrier can be in the form of powders having particle sizes generally in the range of from 20 to 200 microns; if necessary, however, it can be also in the form of pellets.

AlF$_3$ may comprise, besides the gamma and/or beta form, also the delta form, generally also up to amounts of 30% by weight.

Also AlF$_3$ in the alpha form can be present, although it is preferable that the amount thereof should be limited, as this form has proved to be little active.

The catalyst of the invention can be prepared in various manners, one of the preferred methods being the following: the AlF$_3$ carrier in the above-cited crystallographic forms is impregnated, according to one of the conventional techniques of the art, in wet conditions or in dry conditions, with a solution of a soluble salt of trivalent chrome, for example CrCl$_3$·6H$_2$O.

The catalyst is then dried in order to remove the water present therein, then it is charged into a reactor and is subjected to an activation treatment with air or nitrogen either or not in the presence of steam and/or of crystallization water, which can act as an oxidant.

The activation treatment is generally carried out at temperatures ranging from 200° to 600° C., preferably from 350° to 500° C., in order to convert chrome into the oxide form.

The above-cited allotropic structures of AlF$_3$ are known and are characterized by means of the X-ray diffraction spectrum, as is indicated, for example, in J.C.P.D.S. 1981 and in French patent No. 1,383,927 to Du Pont.

The above-considered gammac, deltac and betas phases are the ones described in French patent No. 1,383,927 by J. Cristoph and J. Teufer. The alpha phase is described in Anal. Chem. 29, 984 (1957).

After a long-lasting use, the catalytic activity can be reactivated by means of an air treatment at high temperatures (from 350° to 500° C.).

EXAMPLES

The following examples are given to illustrate the object of the present invention, without being, however, a limitation thereof.

Example 1

Catalyst Preparation

Into an Inconel tubular reactor having a diameter of 8 cm and a length of 100 cm, electrically heated and equipped with a sintered Inconel porous baffle, 1680 g of a catalyst prepared as described hereinafter were charged.

A carrier consisting of AlF$_3$, prevailingly in the gamma form and having a specific surface of 26 m$^2$/g, was impregnated with an aqueous solution of CrCl$_3$·6H$_2$O in the rate of 492 g of CrCl$_3$·6H$_2$O per kg of AlF$_3$.

The solution, consisting of 492 g of CrCl$_3$·6H$_2$O+152 ml of H$_2$O, had a volume of 450 ml and was added to AlF$_3$ in three almost equal portions. After each addition, the catalyst was dried for 4 hours at 120° C. at atmospheric pressure. After the third drying, the catalyst was also sieved and charged into the reactor.

The catalyst was fluidized with a nitrogen stream (about 100 l/h) for 10 hours in the reactor heated to 400° C., then the reactor was brought to the operating temperature.

Example 2

Comparative Test

The above-described reactor was fed, at 380° C., with 1.536 moles/h of trichloroethylene and 9.137 moles/h of anhydrous HF, obtaining a HF/C$_2$HCl$_3$ molar ratio equal to 6 and a contact time of 9.6 seconds, calculated as a ratio between non-fluidized catalyst ratio and volumetric flowrate of the reagents at the reaction temperature and pressure (the pressure was slightly higher than the atmospheric pressure). The gases leaving the reactor were drawn for 1 hour; after absorption of HCl and HF in water and washing of the reaction product with a NaOH aqueous solution, 182 g of a product were recovered, the molar composition of which was as follows:

CF$_3$CH$_2$Cl 87.9%
CF$_3$CH$_2$F 2.0%
C$_2$HCl$_3$ 4.9%

The balance was prevailingly composed of CF$_3$CHF$_2$ and CF$_3$CH$_3$. The conversion of C$_2$HCl$_3$ was of 95.1% and the selectivity in CF$_3$CH$_2$Cl was of 92.4%, while the selectivity in CF$_3$CH$_2$F was of 2.1%. These results were obtained, without any variations, for about 50 hours of run, whereafter the catalyst activity began to decay.

Example 3

The above-described reactor was fed, at 350° C. and at a slightly higher pressure than the atmospheric pressure, with 0.072 moles/h of C$_2$HCl$_3$, 0.62 moles/h of CF$_3$CH$_2$Cl and 3.814 moles/h of anhydrous HF, so obtaining a contact time of 19.5 seconds, a HF/organic product molar ratio equal to 5.5 and an amount of C$_2$HCl$_3$ on the total organic product equal to 10.4%.

Operating as in example 2, 80 g of a product were recovered, the molar composition of which was as follows:

CF$_3$CH$_2$Cl 82.1%
CF$_3$CH$_2$F 16.5%

The balance consisted of little amounts of CF$_2$=CHCl, CHCl=CCl$_2$, CF$_3$CHF$_2$ and CF$_3$CH$_3$. The trichloroethylene conversion was almost quantitative, the total conversion was of 17.7% and the selectivity in CF$_3$CH$_2$F was equal to 93.2%.

Example 4

Into the above-described reactor and under the conditions of example 3, 0.194 moles/h of C$_2$HCl$_3$, 1.010 moles/h of CF$_3$CH$_2$Cl and 7.403 moles/h of anhydrous HF were charged, thereby obtaining a contact time of 10.2 seconds, a HF/organic product ratio of 6.2 and a C$_2$HCl$_3$ amount on the total organic product equal to 16.1%.

Operating in like manner as the preceding examples, 140 g of a product were obtained, the molar composition of which was as follows:

CF$_3$CH$_2$Cl 85.0%
CF$_3$CH$_2$F 13.6%.

The by-products were the same as in example 3.

The trichloroethylene conversion was almost quantitative, the total conversion was equal to 14.5% and the selectivity in CF$_3$CH$_2$F was of 93.8%.

Example 5

Into the above-described reactor and under the conditions of example 3 there were charged 0.250 moles/h of C$_2$HCl$_3$, 0.714 moles/h of CF$_3$CH$_2$Cl and 7.468 moles/h of anhydrous HF, thereby obtaining a contact time of 10.4 seconds, a HF/organic product ratio equal to 7.8 and a C$_2$HCl$_3$ amount on the total organic product equal to 25.9%. Operating in like manner as in the preceding examples it was possible to obtain 112 g of a product, the molar composition of which was as follows:

$CF_3CH_2Cl$ 86.9%
$CF_3CH_2F$ 11.8%
The by-products were the same as in example 3.
The trichloroethylene conversion was almost quantitative, the total conversion being equal to 12.9% and the selectivity in $CF_3CH_2F$ being equal to 91.5%. Under these conditions as well as under the ones of the preceding examples, the catalyst activity did not exhibit an appreciable decay after about a 200-hour run.

Example 6

The reactor of the preceding examples was converted into a plant capable of operating continuously, by addition of a separation column where the light products, including 134a ($CF_3CFH_2$), were drawn, while $CF_3CH_2Cl$ and the higher-boiling products were conveyed to a pump and fed again to the reactor, along with fresh trichloroethylene and HF, in order to make up for the consumptions.
The amount of fresh make-up products underwent slight variations in the time in order to maintain constant the trichloroethylene/$CF_3CH_2Cl$ and HF/organic product ratios. The reference conditions were:
reaction temperature=350° C.; contact time=10 seconds; HF/organic product ratio=6; trichloroethylene/$CF_3CH_2Cl$ ratio=15/85 at the reactor inlet.
After the plant had been adjusted to the operating conditions with a trichloroethylene/$CF_3CH_2Cl$ mixture prepared in advance, there were fed, in 6 hours, 1.08 moles of fresh trichloroethylene and 4.50 moles of fresh anhydrous HF, while about 1 mole of $CF_3CH_2F$ and little amounts of by-products of the same nature as the ones cited in the preceding examples were drawn from the top of the distillation column.

What is claimed is:

1. A process for preparing 1,1,1,2-tetrafluoroethane which comprises reacting, in the gas phase, trichloroethylene with 1,1,1-trifluorochloroethane and hydrofluoric acid, operating with trichloroethylene/1,1,1-trifluorochloroethane molar ratios ranging from 5/95 to 50/50 and in the presence of catalysts comprising $Cr_2O_3$ carried on $AlF_3$ the activity of which catalyst does not appreciably decay during at least about 200 hours of use in the process.

2. The process of claim 1 wherein the reaction is carried out at a temperature of from 300° to 400° C.

3. The process of claim 1 wherein the reaction is carried out at a temperature of from 330° to 380° C.

4. The process of claim 1 wherein the contact time of the reagents ranges from 1 to 50 seconds.

5. The process of claim 1 wherein the contact time of the reagents ranges from 5 to 20 seconds.

6. The process of claim 1 wherein the $AlF_3$ exhibits a specific surface area of from 25 to 30 $m^2/g$.

7. The process of claim 1 carried out continuously.

8. The process of claim 1 wherein the $AlF_3$ is in the gamma and/or beta form.

9. The process of claim 1 wherein the $AlF_3$ comprises principally the gamma form.

10. The process of claim 1 wherein the molar ratio of hydrofluoric acid to (trichloroethylene plus 1,1,1-trifluorochloroethane) is at least 3/1.

11. The process of claim 1 wherein the reaction is carried out in a reaction zone and the process further comprises separating the 1,1,1,2-tetrafluoroethane leaving the reaction zone from other reaction products leaving the reaction zone, recycling the other reaction products to the reaction zone, and restoring the molar ratio of trichloroethylene to 1,1,1-trifluorochloroethane of from 5/95 to 50/50 by the addition of trichloroethylene.

12. A process for the preparation of 1,1,1,2-tetrafluoroethane comprising the steps:
   (a) reacting, in the gas phase in a reaction zone, trichloroethylene with 1,1,1-trifluorochloroethane and HF, operating with trichloroethylene/1,1,1-trifluorochloroethane molar ratios ranging from 5/95 to 50/50 and with HF/(trichloroethylene+1,1,1-trifluorochloroethane) molar ratios of at least 3/1 and in the presence of a catalyst comprising $Cr_2O_3$ carried on $AlF_3$ the activity of which catalyst does not appreciably decay during at least about 200 hours of use in the process, to produce reaction products including 1,1,1,2-tetrafluoroethane;
   (b) separating the 1,1,1,2-tetrafluoroethane from other reaction products leaving the reaction zone; and
   (c) recycling the other reaction products to the reaction zone and restoring the molar ratios defined in step (a) by the addition of trichloroethylene and HF.

13. The process of claim 12 wherein the reaction is carried out at a temperature of from 300° to 400° C.

14. The process of claim 12 wherein the reaction is carried out at a temperature of from 330° to 380° C.

15. The process of claim 12 wherein the contact time of the reagents ranges from 1 to 50 seconds.

16. The process of claim 12 wherein the contact time of the reagents ranges from 5 to 20 seconds.

17. The process of claim 12 wherein the $AlF_3$ exhibits a specific surface area of from 25 to 30 $m^2/g$.

18. The process of claim 12 wherein the $AlF_3$ is in the gamma and/or beta form.

19. The process of claim 12 wherein the $AlF_3$ comprises principally the gamma form.

20. The process of claim 12 wherein the reaction is carried out at a temperature of from 300° to 400° C., the contact time of the reagents ranges from 1 to 50 seconds, the $AlF_3$ exhibits a specific surface area of from 25 to 30 $m^2/g$, and the $AlF_3$ is in the gamma and/or beta form.

* * * * *